United States Patent [19]
Boser et al.

[11] Patent Number: 5,676,694
[45] Date of Patent: Oct. 14, 1997

[54] MEDICAL ELECTRICAL LEAD

[75] Inventors: Gregory A. Boser, Richfield; Mark A. Hjelle, White Bear Lake; Timothy G. Laske, Shoreview; Mark Mabel, Fridley; Pedro A. Meregotte, Coon Rapids; Jon M. Ocel, New Brighton; Clare E. Padgett; David G. Schaenzer, both of Minneapolis; Bret R. Shoberg, Corcoran; Sandra F. Viktora, Coon Rapids, all of Minn.

[73] Assignee: Medtronic, Inc., Minneapolis, Minn.

[21] Appl. No.: 657,577

[22] Filed: Jun. 7, 1996

[51] Int. Cl.$^6$ .................. A61N 1/05; A61B 5/042
[52] U.S. Cl. ............................. 607/122; 128/642
[58] Field of Search ....................... 607/116, 119, 607/122, 123, 148; 128/642

[56] References Cited

U.S. PATENT DOCUMENTS

| | | |
|---|---|---|
| 4,071,070 | 1/1978 | Holleman . |
| 4,161,952 | 7/1979 | Kinney . |
| 4,481,953 | 11/1984 | Gold . |
| 4,603,705 | 8/1986 | Speicher . |
| 4,860,769 | 8/1989 | Fogarty . |
| 4,934,049 | 6/1990 | Kiekhafer . |
| 5,115,818 | 5/1992 | Holleman et al. ............ 607/122 |
| 5,246,014 | 9/1993 | Williams . |
| 5,265,623 | 11/1993 | Kroll . |
| 5,269,319 | 12/1993 | Schulte . |
| 5,343,865 | 9/1994 | Gardineer . |
| 5,347,708 | 9/1994 | Bischoff . |
| 5,366,496 | 11/1994 | Dahl . |
| 5,383,922 | 1/1995 | Zipes . |
| 5,466,254 | 11/1995 | Helland ........................ 607/123 |
| 5,522,872 | 6/1996 | Hoff ............................ 607/119 |
| 5,571,163 | 11/1996 | Helland ........................ 607/123 |

FOREIGN PATENT DOCUMENTS

2157954  11/1985  United Kingdom .............. 607/122

*Primary Examiner*—Jeffrey R. Jastrzab
*Attorney, Agent, or Firm*—Reed A. Duthler; Harold R. Patton

[57] ABSTRACT

A medical electrical lead having an elongated lead body provided with an internal longitudinally extending lumen carrying an elongated stranded or cabled conductor and an electrode coil, located on said lead body. The coil is coupled to the conductor by a conductive sleeve having a tubular portion which has an internal lumen through which the conductor passes and a groove or bore which engages only a portion of a turn or turns of the electrode coil, such that the coil is oriented generally perpendicular to the internal lumen of said sleeve and to the conductor.

8 Claims, 5 Drawing Sheets

MEDICAL ELECTRICAL LEAD

BACKGROUND OF THE INVENTION

The present invention relates to implantable medical electrical leads, and more particularly relates to implantable leads of the type provided with coil electrodes.

Implantable defibrillation leads, especially transvenous leads, typically employ elongated coils as electrodes. These electrode coils are coupled at one or both ends to an elongated conductor extending through the lead body to the electrode. Transvenous pacing leads, cardiac ablation catheters and other electrode bearing leads and catheters may also employ coil electrodes. Over the years, quite a large number of different mechanisms for interconnecting coil electrodes and conductors have been proposed including welding, crimping, and swaging. It is desirable that such connections between the conductor and the electrode provide a highly reliable electrical connection, with good mechanical properties including high tensile strength. It is also desirable that such connections allow for the lead assembly itself to retain a high degree of tensile strength through the area of the electrode.

Typically, conductors in commercially marketed pacing and defibrillation leads have taken the form of single or multifilar wire coils. However, there has been a high level of interest recently in pacing and defibrillation leads employing stranded wire conductors such as cables, instead of coiled wire conductors. Such stranded conductors present a new set of requirements for interconnection with electrode coils, if the above described design goals are to be accomplished.

SUMMARY OF THE INVENTION

The present invention is directed toward accomplishing the goal of a reliable, high strength connection between a stranded or cabled conductor and a coil electrode, particularly in the context of an implantable lead. The present invention addresses these goals by means of a crimp sleeve which includes a tubular portion intended to be slid over and crimped to a stranded or cabled conductor, and means located on the tubular portion for allowing interconnection to a portion of one or more turns of an electrode coil. In the case of multifilar or multiple coil electrodes, connection is made to a portion of one or more turns of each filar or coil. The means for interconnecting the electrode coil can either be a bore or a groove, running essentially perpendicular to the lumen of the tubular portion through which the conductor passes. Interconnection of the electrode coil to a weld/crimp sleeve provided with a bore may be made by passing a portion of a turn of the electrode coil through the bore, and welding or brazing the coil to the bore at the entry and exit points thereof. Alternatively the connection may be made by staking or otherwise compressing the bore to engage the coil. Interconnection of the electrode coil to a crimp sleeve provided with a groove may be made by either laying a portion of a turn of the electrode coil in the groove or by passing a portion of a turn of the electrode coil along the groove, and then welding or brazing the electrode coil to the sleeve along with the groove. Alteratively the connection may be made by staking or otherwise compressing the groove to engage the coil.

The tubular portion of the sleeve is sized so that it is locatable in the lumen in the lead body which carries the stranded or cabled conductor. In some embodiments, the bore or groove is located on a protrusion extending radially outward from the tubular portion of the sleeve, so that protrusion may extend outside of the lead body when the tubular portion is located within the internal lumen carrying the conductor, facilitating easier assembly and the welding or brazing procedure. The location of the bore or groove on such a protrusion also allows the electrode coil to be connected to the sleeve without any distortion of the electrode coil and avoids damage to the insulation and conductor. The cylindrical portion of the sleeve may be attached to the conductor by means of a plurality of crimps, spaced around the circumference of the tubular portion of the sleeve.

By means of this invention, a reliable mechanical connection is provided to a stranded or cabled conductor, and the electrode coil may be connected therewith with minimal deformation. The orientation of the coil wire generally perpendicular to the conductor results in increased resistance to flex fatigue as compared to other orientations. The configuration of the sleeve also allows the to continue uninterrupted through the attachment points of the electrode coil and the resulting structure is highly resistant to mechanical failure even in the event that the lead body is stretched substantially.

DETAILED DESCRIPTION OF THE PREFERRED EMBODIMENTS

The illustrated embodiments of the present invention are practiced in defibrillation leads which have multi-lumen lead bodies generally as disclosed in pending, commonly assigned U.S. patent application No. 08/438,125, filed May 8, 1995 by Shoberg et al now U.S. Pat. 5,584,873, incorporated herein by reference in its entirety. However, the present invention may also be usefully employed other types of leads and catheters such as cardiac pacing leads, nerve and muscle stimulation leads, ablation catheters and other electrode bearing leads and catheters having lead bodies and conductors of differing types.

Figure 1:
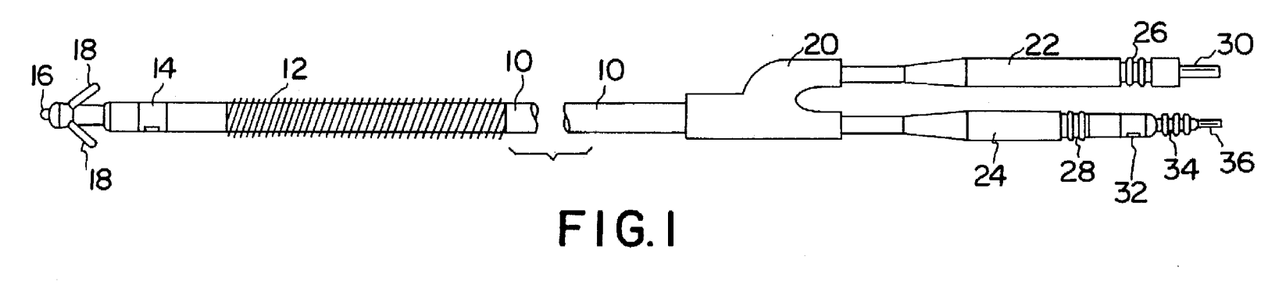
FIG. 1 is a plan view of an implantable lead in which a first embodiment of the present invention is practiced.

FIG. 1 is a plan view of a defibrillation lead in which the present invention is practiced. The lead of FIG. 1 is provided with an elongated insulative lead body 10, preferably fabricated of silicone rubber, polyurethane or other biocompatible polymer. At the distal end of the lead, it carries an elongated defibrillation electrode coil 12, a ring electrode 14 and a tip electrode 16, each coupled to a conductor located within the lead body 10. Tines 18 are provided for maintaining electrode 16 in contact with the tissue of the right ventricle. Electrodes 16, 14 and 12 may correspond to any conventionally available pacing and defibrillation electrodes.

The proximal end of the lead carries a connector assembly, beginning with a molded lead bifurcation 20, which splits off two of the conductors within lead body 10 to a bipolar, in-line connector assembly 24, generally corresponding to the IS-1 connector standard for pacing leads. Connector assembly 24 is provided with a first set of sealing rings 28; a connector ring 32, a second sealing rings 34 and connector pin 36. Connector pin 36 is coupled to the conductor which extends through the lead body 10 to tip electrode 16. Connector ring 32 is coupled to the conductor which extends through the lead body 10 to ring electrode 14. The conductor coupled to defibrillation electrode 12 extends into connector assembly 22, which carries a set of sealing rings 26 and a connector pin 30, coupled to the conductor extending through lead body 10 to defibrillation electrode 12. The illustrated connector assemblies are conventional elements, and may correspond to any of the numerous known electrical connector assemblies provided on implantable medical leads.

Although not visible in FIG. 1, the conductor coupling connector pin 36 to electrode 16 takes the form of a multifilar coiled conductor to allow passage of a stylet therethrough, while the conductors coupling ring electrode 14 to connector ring 32 and coupling defibrillation electrode 12 to connector pin 30 take the form of a cable fabricated of bundled, stranded wires and provided with a coating of PTFE.

Figure 2:
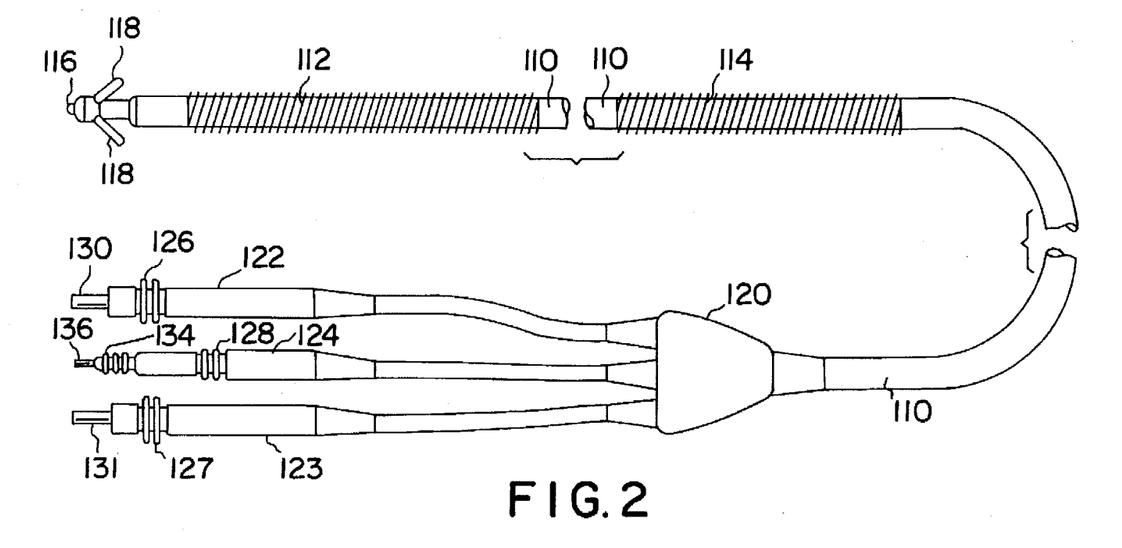
FIG. 2 is a plan view of an implantable lead in which a second embodiment of the present invention is practiced.

FIG. 2 is a plan view of a second defibrillation lead in which an alterative embodiment of the present invention is practiced. The lead of FIG. 2 is also provided with an elongated insulative lead body 110, preferably fabricated of silicone rubber, polyurethane or other biocompatible polymer. At the distal end of the lead, it carries an elongated distal defibrillation electrode coil 112, an elongated proximal defibrillation electrode coil 114 and a tip electrode 116, each coupled to a separate conductor located within the lead body 110. Tines 118 are provided for maintaining electrode 16 in contact with the tissue of the right ventricle. Electrodes 112, 114 and 116 may correspond to any conventionally available pacing and &fibrillation electrodes.

The proximal end of the lead carries a connector assembly, beginning with a molded lead trifurcation 120, which splits off one conductor within lead body 110 to a unipolar, in-line connector assembly 124, generally corresponding to the IS-1 connector standard for pacing leads. Connector assembly 124 is provided with a first set of sealing rings 128, a second set of sealing rings 134 and a connector pin 136. Connector pin 136 is coupled to the conductor which extends through the lead body 110 to tip electrode 116. Connector assembly 122 carries a set of sealing rings 126 and a connector pin 130, coupled to the conductor extending through lead body 110 to defibrillation electrode 112. Connector assembly 123, carries a set of sealing rings 127 and a connector pin 131, coupled to the conductor extending through lead body 110 to defibrillation electrode 114. The illustrated connector assemblies are conventional elements, and may correspond to any of the numerous known electrical connector assemblies provided on implantable medical leads.

Although not visible in FIG. 1, the conductor coupling connector pin 136 to electrode 116 takes the form of a multifilar coiled conductor to allow passage of a stylet therethrough, while the conductor coupling defibrillation electrode 114 to connector pin 131 and the conductor coupling defibrillation electrode 112 to connector pin 130 take the form of cables fabricated of bundled, stranded wires and provided with a coating of PTFE.

The particular configuration of the PTFE insulated, bundled stranded conductor cables employed in the illustrated embodiments of the invention may correspond, for example, to the conductors disclosed in the above-cited Shoberg application or in U.S. Pat. No. 5,246,014, issued to Williams et al, also incorporated herein by reference in its entirety However other conductors, and particularly other stranded or cabled conductors as known to the art may also be employed.

Figure 3:
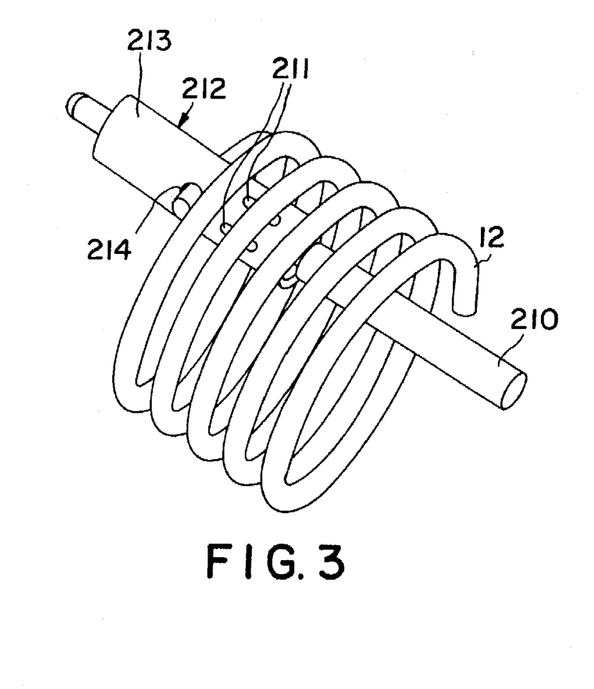
FIG. 3 is a perspective drawing illustrating the interconnection between the coil electrode and the conductor cable of the lead illustrated in FIG. 1.

FIG. 3 illustrates the interconnection of an electrode coil 12 illustrated in FIG. 1 with an insulated conductor cable 210, by means of a crimp sleeve 212 according to the present invention. Sleeve 212 is fabricated of a conductive biocompatible metal such as titanium, stainless steel, tantalum or platinum, as is electrode coil 12. Insulation on conductor 210 is first stripped away in the area in which the sleeve 212 is to be located. The bared conductor is then inserted into the longitudinal lumen through the tubular portion 213 of sleeve 212 and the tubular portion is attached to the conductor by means of a plurality, e.g. 4, of crimps 211 spaced around the circumference of the tubular portion 213 of the sleeve. The end portion of the proximal or distal turn of electrode coil 12 is then passed through a bore 214, which is generally perpendicular to the lumen through the tubular portion of the sleeve. Coil 12 is then welded or brazed to sleeve 212 at the entry and exit points of the coil to provide a reliable interconnection. As noted above, the sleeve alternatively may be staked or compressed to hold the coil 12 in place. A more detailed description of how this process is undertaken in the context of assembly of the lead is included in conjunction with the description of FIGS. 9–11, below.

Figure 4:
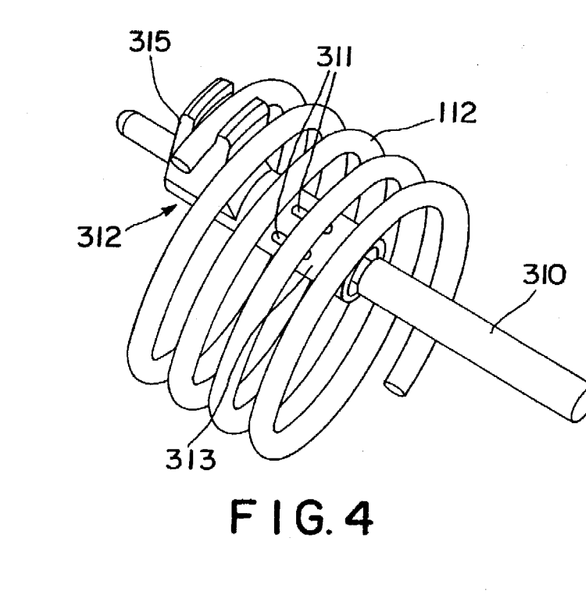
FIG. 4 is a perspective drawing illustrating the interconnection between the coil electrode and the conductor cable of the lead illustrated in FIG. 2.

FIG. 4 shows the interconnection of the electrode coil 112 of the lead illustrated in FIG. 2 to an insulated conductor cable 310. Similar to FIG. 3, the conductor 310 is stripped of insulation in the area which passes through sleeve 312, and the tubular portion 313 of the sleeve 312 is crimped to the bared conductor by means of crimps 311. Thereafter, a portion of the distal or proximal turn of conductor coil 112 is laid in groove 313 of the sleeve, and is welded or brazed to the sleeve by means of a laser weld extending along groove 314. As noted above, the sleeve alternatively may be staked or compressed to hold the coil 12 in place. A more detailed description of how this process is undertaken in the context of assembly of the lead is included in conjunction with the description of FIGS. 9–11, below.

Figures 5, 7:
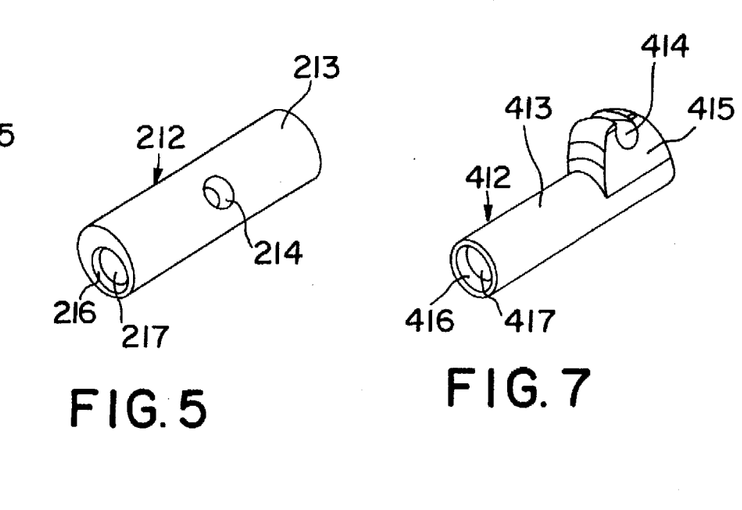
FIG. 5 is a perspective drawing illustrating the crimp sleeve employed to couple the coil electrode and the conductor cable of the lead illustrated in FIG. 1.
FIG. 7 is a perspective drawing illustrating of an alternative embodiment of the crimp sleeve employed to couple the coil electrode and the conductor cable of the lead illustrated in FIG. 2.

FIG. 5 illustrates sleeve 212, and its associated cross bore 214. The tubular portion 213 of sleeve 212 is provided with a longitudinal lumen 217, which intersects cross bore 214. Sleeve 212 is provided with an internal, circumferential chamfer at each end of the tubular portion of the sleeve, one of which is visible at 216. external chamfers or rounds may also be provided to ease assembly and reduce possibilities of damage to the conductor and the lead body. The internal chamfers provide for stress relief at the entry and exit points of the conductor. The internal chamfers also assist in preventing damage to the insulated conductor as it is passed through the longitudinal lumen of the sleeve during assembly.

Figure 6:
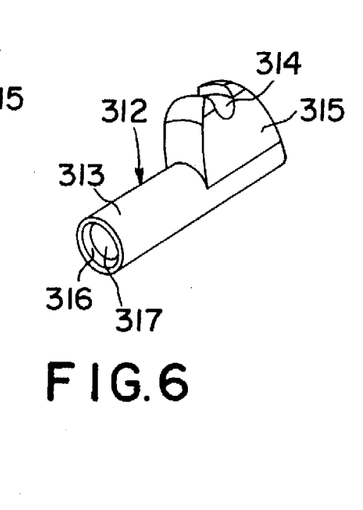
FIG. 6 is a perspective drawing illustrating the crimp sleeve employed to couple the coil electrode and the conductor cable of the lead illustrated in FIG. 2.

FIG. 6 illustrates sleeve 312, including groove 314, which runs perpendicular to the longitudinal lumen 317 through the tubular portion 313 of the sleeve 312. Similar to the sleeve illustrated in FIG. 5, the sleeve 312 is provided with internal circumferential chamfers at both ends, of which one is visible at 316. External chamfers or rounds may also be provided at each end. Groove 314 is located on a protrusion 315, which extends radially outward from the tubular portion of the sleeve.

FIG. 7 shows a first, alternative embodiment to the sleeve of FIG. 6, in which the groove, 414 also runs perpendicular to the tureen 417 through the tubular portion 413. Groove 414 is narrower at its outer portion than the diameter of the electrode coil to be located therein. Therefore, the electrode coil is passed through the groove 414 longitudinally, much as it would be threaded through a cross-bore. However, interconnection is done by means of a laser weld or braze along the groove, as in conjunction with the sleeve of FIG. 6. The narrower groove results in improved thermal contact between the coil and sleeve during welding or brazing. As in the sleeves of FIGS. 5 and 6, internal chamfers are provided at both ends of the tubular portion 313 of the sleeve, of which one is visible at 416. Groove 414 is located on a protrusion 415, which extends radially outward from the tubular portion 313 of the sleeve.

Figure 8:
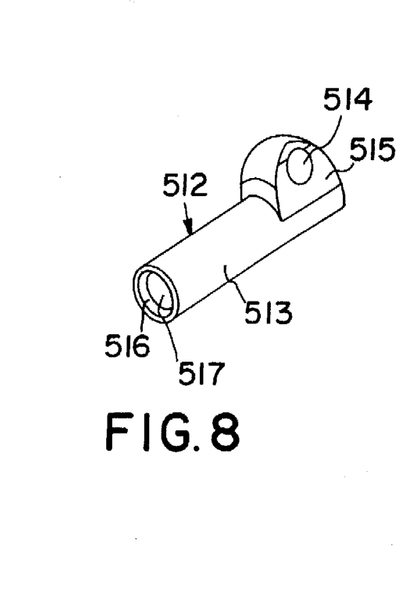
FIG. 8 is a perspective drawing illustrating of an additional alternative embodiment of the crimp sleeve employed to couple the coil electrode and the conductor cable of the lead illustrated in FIG. 2.

FIG. 8 shows yet another alternative embodiment to a sleeve of FIG. 6. Sleeve 512 is provided with a cross-bore 514 which is perpendicular to but does not does not intersect the longitudinal lumen 517 through the tubular portion 513 of the sleeve. Interconnection is made in the same fashion as with the sleeve of FIG. 5, with welding at the entry and exit points of the electrode coil. Internal chamfers are provided at the proximal and distal end of the sleeve 512, which one is visible at 516. Bore 514 is located on a protrusion 515, which extends radially outward from the tubular portion of the sleeve.

Figure 9:
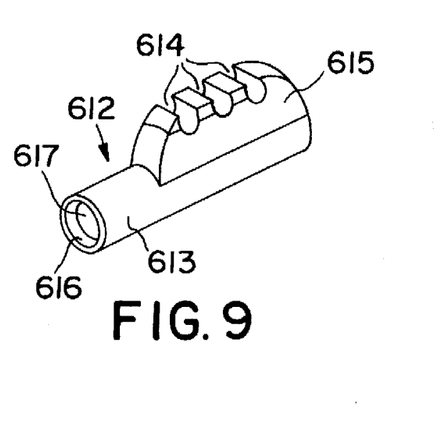
FIG. 9 is a perspective drawing illustrating of an alternative embodiment of the crimp sleeve which may be employed to couple a multi-filar coil electrode and a conductor cable.

FIG. 9 shows an embodiment of a sleeve similar to that of FIG. 6, but adapted to engage either multiple turns of a single coil or portions of a single turn of each of a plurality of coils. Sleeve 612 is provided with multiple cross-grooves 614 which are perpendicular to longitudinal lumen 617 through the tubular portion 613 of the sleeve. Interconnection is made in the same fashion as with the sleeve of FIG. 6. Internal chamfers are provided at the proximal and distal end of the sleeve 612, which one is visible at 616. Grooves 614 are located on a protrusion 615, which extends radially outward from the tubular portion of the sleeve.

Figure 10:
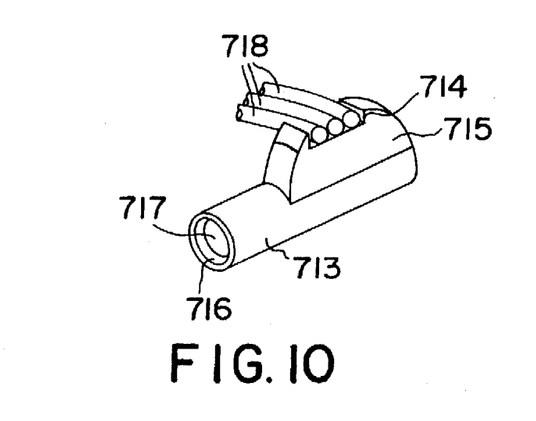
FIG. 10 is a perspective drawing illustrating of an additional alternative embodiment of the crimp sleeve which may be employed to couple a multi-filar coil electrode and a conductor cable.

FIG. 10 shows an alternative embodiment of a sleeve similar to that of FIG. 6, but adapted to engage either multiple turns of a single coil or portions of a single turn of each of a plurality of coils. Sleeve 712 is provided with a single, wider cross-groove 714 which is perpendicular to longitudinal lumen 717 through the tubular portion 713 of the sleeve and which is wide enough to permit portions of a plurality of turns 718 of one or more electrode coils to be laid therein. Interconnection is made by welding along the edges of the groove 714 and by welding the portions of the coils located therein to one another. Internal chamfers are provided at the proximal and distal end of the sleeve 712, which one is visible at 716. Groove 714 is located on a protrusion 715, which extends radially outward from the tubular portion of the sleeve.

Figure 11:
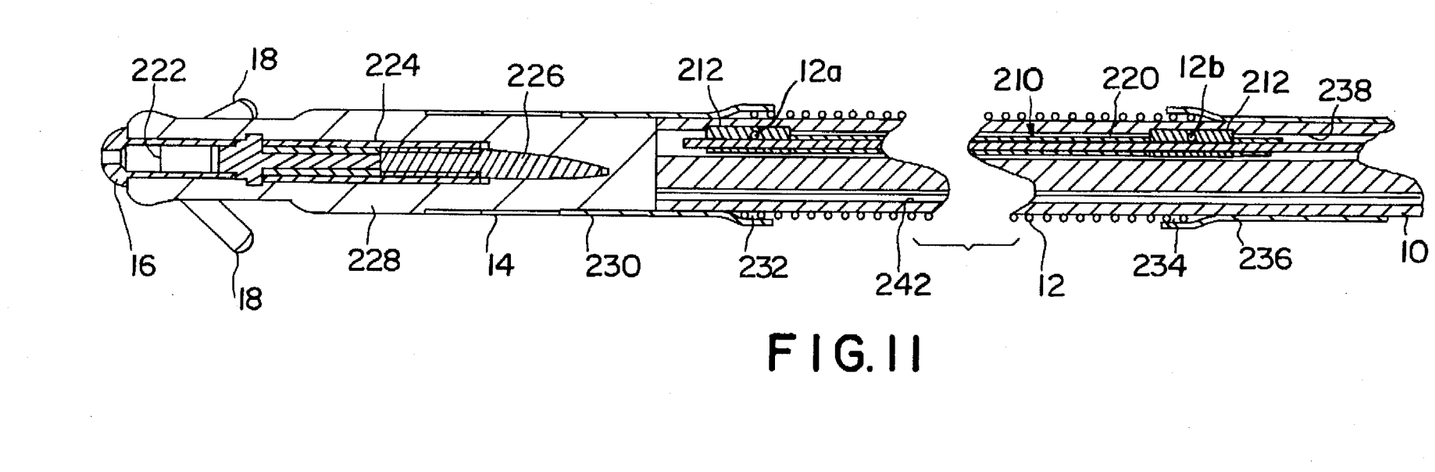
FIG. 11 is a sectional view through the lead illustrated in FIG. 1, in the vicinity of the coil electrode.

FIG. 11 is a sectional view through the distal portion of the lead illustrated in FIG. 1, including the area of electrode 12. In this view, the interrelation of the insulated conductor cable 210, lead body 10 and sleeves 212 is more readily apparent. Conductor 210 passes through an internal lumen 238 within lead body 10, and has its insulation 220 removed in areas in which it passes through the sleeves 212, so that direct electrical connection can be made to the conductor cable 218 located therein. In this view, the distal and proximal turns of electrode coil 12 can be seen at 12A and 12B, respectively, as they pass through the perpendicular bores through sleeves 212. The sleeves 212 are first crimped to the conductor cable and the cable is then passed through lumen 238. Areas of the outer wall of lead body 10 exterior to sleeves 212 are slit and the lead body is bent to widen the slit and expose the cross bores through the sleeves. Portions of the proximal end and distal turns of electrode coil 12 are then inserted through the cross bores in the sleeves and the entry and exit points of the coil are laser welded to the sleeve. Thereafter, external polymeric sleeves 230 and 236, respectively are slid over the distal and proximal ends of conductor coil 12, and the areas between the sleeves 230 and 236 are backfilled by means of medical adhesive or other polymeric material at 232 and 234, to further anchor the proximal and distal ends of the electrode coil. The electrode coil 12 may be secured to the outer circumference of the lead body 10 by means of a backfilling process as described in U.S. Pat. No. 4,934,049, incorporated herein by reference in its entirety.

Extending distally from the defibrillation electrode 12, the lead takes the form of a molded piece part 228, which carries ring electrode 14, coupled to a conductor 246 (not visible in this view). Electrode 16 as illustrated is a steroid-eluting electrode, provided with a monolithic controlled release device 222 located within a chamber within the electrode, and the electrode 16 is coupled to a coiled conductor 226 by means of an external crimping sleeve 224. Other types of tip electrodes, including screw-in electrodes may of course be substituted.

Figure 12:
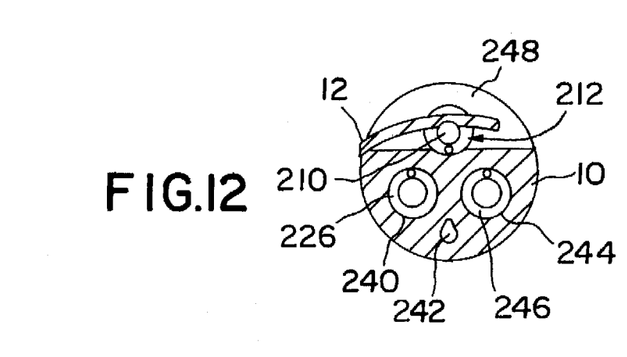
FIG. 12 is a cross sectional view through the lead of FIG. 1, in the vicinity of a crimp sleeve employed to couple the coil electrode and the conductor cable of the lead

FIG. 12 illustrates a cross-section of the lead in the vicinity of one of the crimp sleeves 212. In this view, it can be seen that the lead body 10 is provided with three conductor lumens 238, 240 and 244. Conductor lumen 238 surrounds sleeve 212. In this view it can be seen that a portion of one turn of electrode coil 12 passes through the bore of the sleeve and is in direct contact with conductor cable 220, in addition to being welded to sleeve 212. As described above, prior to the step of passing the end of conductor coil 12 through the bore through sleeve 212, the outer wall of the lead body 10 is slit, at 248 allowing access to the bore. A compression lumen 242, as described in the Shoberg application, cited above, is also visible in this view.

It should be noted that use of sleeve 212 as illustrated has the result that the lead body continues essentially uninterrupted throughout the length of the defibrillation electrode 12, including the proximal and distal end points of the defibrillation electrode. This allows for maintenance of good tensile strength in the lead body structure, throughout the length of the defibrillation electrode and avoids any possible fluid leakage paths between lumens in the lead body. The use of sleeve 212 also results in a structure which allows for a multiple-lumen lead body of small cross section while still providing adequate insulation thickness. Because the interconnection of the coil to the conductor does not require a rigid metal component extending around the entire circumference of the lead, a greater degree of flexibility throughout the attachment points of the electrode coil to the conductor results. It should also be noted that the tensile strength of the connection between the electrode coil and the conductor is such that in the event that a lead body is stretched with respect to the conductor cable 210, which is essentially inelastic, sleeves 212 will simply be pulled proximally within the lead body, pulling the proximal and distal ends of the electrode 212 into the lumen 238, without interrupting the electrical or mechanical interconnection of the two structures. While the movement of electrode coil 212 into the lumen may result in the creation of fluid leakage paths, it is much preferable to a gross rupture of the lead insulation or breaking of the connection between the conductor and the electrode coil, as might otherwise occur. Thus, the resulting structure overall is capable of continued functioning even after damage due to applied tensile forces.

Figure 13:
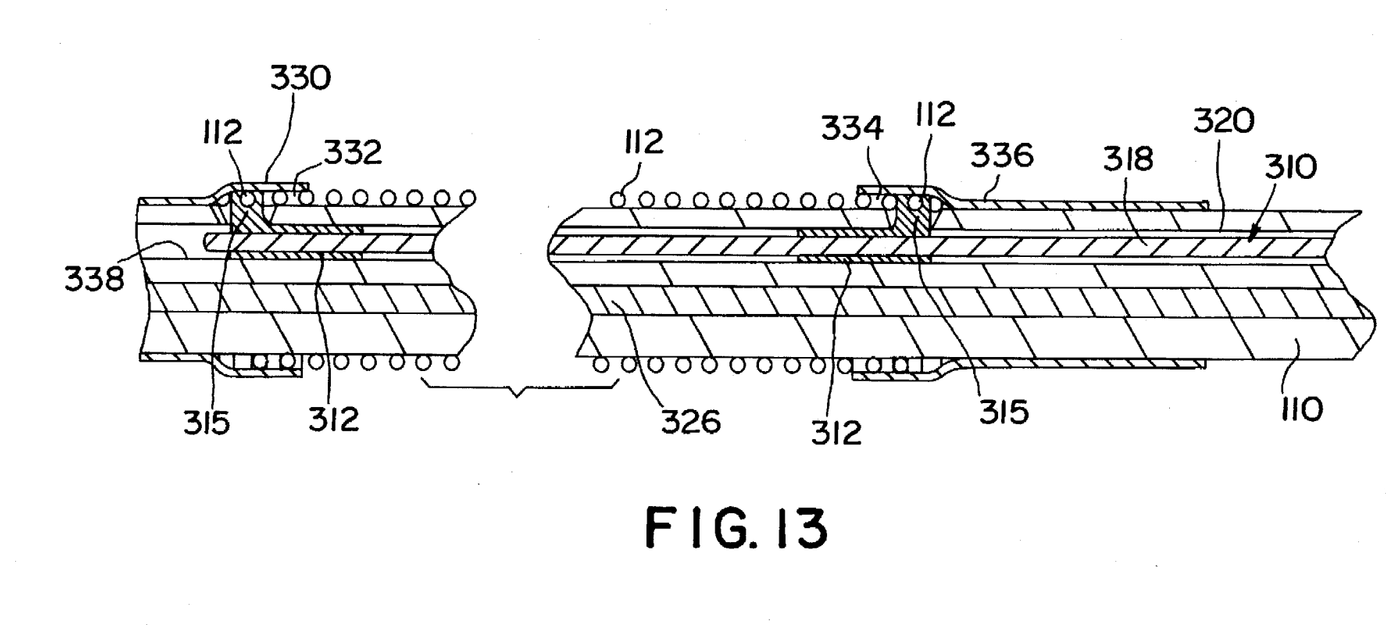
FIG. 13 is a sectional view through the lead illustrated in FIG. 2, in the vicinity of the coil electrode.

FIG. 13 shows a sectional view through the lead of FIG. 2 in the vicinity of the defibrillation electrode 112. In this view, the interrelation of the sleeves 312 and the insulated electrical cable 310 is visible. As in conjunction with the structure illustrated in FIG. 9, the portions of conductor 310 which are to be located within the sleeves 312 are first stripped of the insulation 318, so that the tubular portions of the sleeves can be crimped directly to the conductor cable 316. In this case, the portions of sleeve 312 which are provided with the perpendicular grooves 314 extend outward on projections, through the outer wall of lead body 110, such that the proximal and distal turns 112A and 112B, respectively of the electrode coil can simply be laid into the grooves, followed by laser welding along the lengths of the grooves to secure the electrode coil 112 to the sleeves 312. Extension of the grooves radially outward of the lead body insulation is particularly beneficial in facilitating assembly of the coil to the sleeve, the welding or brazing operation and the visual inspection thereof. In addition, spacing the weld or braze sit outward and away from the conductor assists in avoiding damage to the conductor during the welding or brazing operation. These same benefits are realized if the sleeves of FIGS. 7, 8, 9 or 10 are substituted for sleeves 312.

Prior to the connection of the electrode 112 to the sleeves 312 and laser welding, the outer wall of the lead body 110 is cut away in the area in which the protrusions of sleeves 312 will be located. Following laser welding or brazing, the removed material is replaced by adhesive, polymeric sleeves 330 and 334 are placed over the proximal and distal ends of the electrode coil 112, and the areas 332 and 334 therein are backfilled with adhesive to anchor the proximal and distal ends of the electrode coil, as discussed above. Also visible in FIG. 13 is the coiled conductor 326, which extends through the lead body, to the tip electrode 116 (not visible in this view.)

The structure of the lead illustrated in FIG. 13, like the structure of FIGS. 11 and 12 provides for a lead having a high degree of tensile strength throughout the length of defibrillation electrode 312, due to the fact that the lead body 110 is continuous throughout the electrode area. Provision of grooves located on projections which extend radially outward of the tubular portions the sleeves facilitates laser welding and avoids any required deformation of the electrode coil 112 in conjunction with interconnecting the coil to the conductor, and is believed to enhance the reliability of the entire structures.

In conjunction with the above disclosure, we claim:

1. A medical electrical lead comprising:
an elongated lead body provided with an internal longitudinally extending lumen and having a circumference;
an elongated conductor located in and extending along said lumen of said lead body;
an electrode coil having a plurality of turns, extending circumferentially around said lead body;
a conductive sleeve having a tubular portion located in the lumen of the lead body and which has an internal lumen through which said conductor passes, said conductor being coupled electrically to said sleeve, said sleeve further having means for engaging only a portion of a only a single said turn of said electrode coil, such that said portion of said turn of said coil passes generally perpendicular to said internal lumen of said sleeve, said portion extending circumferentially along said turn of said coil for less than one full turn.

2. A lead according to claim 1 wherein said engaging means comprises a groove formed in said sleeve, generally perpendicular to said internal lumen of said sleeve.

3. A medical electrical lead comprising:
an elongated lead body provided with an internal longitudinally extending lumen;
an elongated conductor located in and extending along said lumen of said lead body;
an electrode coil having a plurality of turns, located on said lead body;
a conductive sleeve comprising a tubular portion located in said lumen of said lead body and which has an internal lumen through which said conductor passes, said conductor being coupled electrically to said sleeve, said sleeve further having means for engaging only a portion of a said turn of said electrode coil, such that said portion of said turn of said coil passes generally perpendicular to said internal lumen of said sleeve, wherein said engaging means comprises a bore through said sleeve, generally perpendicular to said internal lumen of said sleeve.

4. A medical electrical lead comprising:
an elongated lead body provided with an internal longitudinally extending lumen and having a circumference;
an elongated conductor located in and extending along said lumen of said lead body;
an electrode coil comprising a plurality of turns extending circumferentially around the lead body;
a conductive sleeve comprising a tubular portion located in said lumen of said lead body and which has an internal lumen through which said conductor passes, said conductor being coupled electrically to said sleeve, said sleeve further having means for engaging only a portion of a said turn of said electrode coil, such that said portion of said turn of said coil passes generally perpendicular to said internal lumen of said sleeve, wherein said engaging means comprises means for engaging only a portion of each of a plurality of turns of said electrode coil, each of said portions extending circumferentially along a said turn of said coil for less than one full turn.

5. A lead according to claim 1 or claim 3 or claim 2 or claim 4 wherein said sleeve is provided with a protrusion extending from said tubular portion of said sleeve radially outward to an exterior surface of said lead body and wherein said engaging means is located on said protrusion.

6. A lead according to claim 1 or claim 3 or claim 2 or claim 4 wherein said electrode coil is welded to said sleeve.

7. A lead according to claim 1 or claim 3 or claim 2 or claim 4 wherein said tubular portion of said sleeve is crimped to said conductor.

8. A medical electrical lead comprising:

an elongated lead body provided with an internal longitudinally extending lumen;

an elongated conductor located in and extending along said lumen of said lead body;

an plurality of electrode coils, each having a having a plurality of turns and located on said lead body;

a conductive sleeve comprising a tubular portion located in said lumen of said lead body and which has an internal lumen through which said conductor passes, said conductor being coupled electrically to said sleeve, said sleeve further having means for engaging only a portion of a said turn of said electrode coil, such that said portion of said turn of said coil passes generally perpendicular to said internal tureen of said sleeve, wherein said engaging means comprises means for engaging only a portion of a turn of each of said plurality of electrode coils.

* * * * *

UNITED STATES PATENT AND TRADEMARK OFFICE
CERTIFICATE OF CORRECTION

PATENT NO. : 5,676,694

DATED : October 14, 1997

INVENTOR(S) : Gregory A. Boser, Mark A. Hjelle, Timothy G. Laske, Pedro A. Meregotte, Jon M. Ocel, Clare E. Padgett, David G. Schaenzer, Bret R. Shoberg, Sandra F. Viktora It is certified that error appears in the above-identified patent and that said Letters Patent is hereby corrected as shown below:

Column 10, line 14, delete "tureen" and substitute --lumen-- therefor.

Signed and Sealed this

Seventh Day of April, 1998

Attest:

BRUCE LEHMAN

Attesting Officer

Commissioner of Patents and Trademarks